United States Patent [19]

Sohda et al.

[11] Patent Number: 5,312,824
[45] Date of Patent: May 17, 1994

[54] CERTAIN 2-[(4-DIFLUOROMETHOXY-2-PYRIDYL)-METHYLTHIO OR METHYLSULFINYL-5-BENZIMIDAZOLES USEFUL FOR TREATING PEPTIC ULCERS

[75] Inventors: Takashi Sohda, Takatsuki; Nobuhiro Inatomi, Mishima, both of Japan

[73] Assignee: Takeda Chemical Industries, Ltd., Osaka, Japan

[21] Appl. No.: 777,171

[22] Filed: Oct. 16, 1991

[30] Foreign Application Priority Data

Oct. 17, 1990 [JP] Japan ................................ 2-280331
Jun. 21, 1991 [JP] Japan ................................ 3-149045

[51] Int. Cl.[5] .................. C07D 401/12; C07D 403/12; A61K 31/44
[52] U.S. Cl. ..................................... 514/338; 546/271
[58] Field of Search .................. 546/271, 278; 514/338

[56] References Cited

U.S. PATENT DOCUMENTS

| | | | |
|---|---|---|---|
| 4,255,431 | 3/1981 | Junggren et al. | 514/338 |
| 4,472,409 | 9/1984 | Senn-Bilfinger | 514/338 |
| 4,628,098 | 12/1986 | Nohara et al. | 546/271 |
| 4,689,333 | 8/1987 | Nohara et al. | 514/338 |
| 4,758,579 | 7/1988 | Kohl et al. | 514/338 |

FOREIGN PATENT DOCUMENTS

| | | | |
|---|---|---|---|
| 0208452 | 1/1987 | European Pat. Off. | 546/271 |
| 88/03921 | 6/1988 | World Int. Prop. O. | 546/271 |
| 89/11479 | 11/1989 | World Int. Prop. O. | 546/271 |
| 90/02124 | 3/1990 | World Int. Prop. O. | 546/271 |

*Primary Examiner*—Alan L. Rotman
*Attorney, Agent, or Firm*—Wegner, Cantor, Mueller & Player

[57] ABSTRACT

A compound of the formula

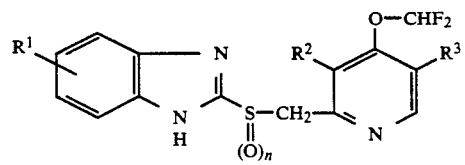

wherein $R^1$ stands for a substituent on benzene ring, $R^2$ and $R^3$ independently stand for hydrogen or methyl, and n denotes 0 or 1, or a pharmacologically acceptable salt thereof is useful for prophylaxis and treatment of peptic ulcers (e.g. gastric ulcer, duodenal ulcer) and gastritis.

11 Claims, No Drawings

CERTAIN 2-[(4-DIFLUOROMETHOXY-2-PYRIDYL)-METHYLTHIO OR METHYLSULFINYL-5-BENZIMIDAZOLES USEFUL FOR TREATING PEPTIC ULCERS

FIELD OF THE INVENTION

The present invention relates to pyridine derivatives useful as e.g. anti-ulcer agents and to a method of producing them.

BACKGROUND OF THE INVENTION

As the pyridine derivatives having anti-ulcer activity, those disclosed in JPA S54(1979)-141783 (the corresponding U.S. Pat. No. 4,255,431), JPA S58(1983)-135881 (the correeesponding U.S. Pat. No. 4,472,409), JPA S61(1986)-50978 (the corresponding U.S. Pat. Nos. 4,628,098 and 4,689,333), etc. have been known.

However, a compound having a gastric mucous membrane protecting action stronger than that of those known compounds has been desired.

It is considered that gastrointestinal ulcer is induced by imbalance between aggressive factors, e.g. acid and pepsin, and defensive factors e.g. mucus secretion and mucosal blood flow. Therefore, a medication having an antisecretory action and an action of enhancing protection of the gastric mucosa has been desired.

The present inventors diligently studied with the purpose of preparing an anti-ulcer agent having excellent actions of inhibiting gastric acid secretion, of protecting gastric mucosa and of antagonizing. They found that a certain type of pyridine derivatives meet the said purpose, and they conducted further study to accomplish the present invention.

SUMMARY OF THE INVENTION

The present invention relates to (1) pyridine derivatives represented by the formula

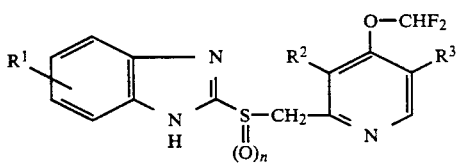

wherein $R^1$ stands for a substituent on the benzene ring, $R^2$ and $R^3$ independently stand for hydrogen or methyl, and n denotes 0 or 1, or their salts. (2) A method of producing a pyridine derivative represented by the formula

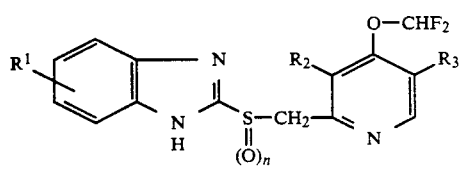

wherein $R^1$, $R^2$, $R^3$, and n are of the same meaning as defined above or a salt thereof, which is characterized by allowing a compound represented by the formula

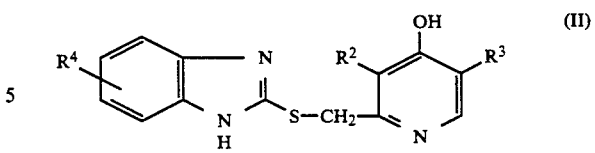

wherein $R^2$, and $R^3$ are of the same meaning as defined above, and $R^4$ stands for a substituent on the benzene ring, to react with chlorodifluoromethane, and when necessary, subjecting the reaction product to oxidation.

DETAILED DESCRIPTION OF THE PREFERRED EMBODIMENT

In the above formula, examples of the substituent on the benzene ring shown by $R^1$ include hydrogen; hydroxyl group; halogen such as fluorine, chlorine, bromine and iodine; difluoromethoxy and trifluoromethyl.

In the above formula, examples of the substituent on the benzene ring shown by $R^4$ include hydrogen; hydroxyl group; halogen such as fluorine, chlorine, bromine and iodine; and trifluoromethyl.

$R^1$ and $R^4$ may be located at 4- or 5-position, and preferably at 5-position.

A sulfide derivative (I) (n=0), among the object compounds of this invention, can be produced by allowing the starting compound (II) to react with chlorodifluoromethane. It is convenient to conduct this reaction in the presence of a base. The base is exemplified by alkali metal hydride e.g. sodium hydride and potassium hydride; alkali metal e.g. metallic sodium; sodium alkoxide e.g. sodium methoxide and sodium ethoxide; alkali metal carbonate e.g. potassium carbonate and sodium carbonate; and organic amines e.g. triethylamine, 1,8-diazabicyclo[5,4,0]undec-7-ene (DBU), and 1,5-diazabicyclo[4,3,0]non-5-ene (DBN). Examples of the solvent to be used for the reaction include alcohols such as methanol or ethanol; ethers such as ether or tetrahydrofuran; and N,N-diemthylformamide, dimethylsulfoxide, etc. The amount of a base to be used for the reaction is usually in a little excess to the equivalent, but it may be in a large excess. Specifically, it is about 1–10 equivalents, more preferably about 1.1–4 equivalents. The reaction temperature ranges usually from about 0° C. to about the boiling point of the solvent used, more preferably from about 20° C. to about 80° C. The reaction time ranges from about 0.2 to about 24 hours, more preferably from about 0.5 to about 2 hours.

When $R^4$ is a hydroxyl group, it can be converted to a difluoromethoxy group by reacting with chlorodifluoromethane. The hydroxyl group at the 4-position of the pyridine ring can be selectively converted to a difluoromethoxy group, since it is more reactive than the hydroxyl group on the benzene ring.

A sulfinyl derivative (I) (n=1), which is also among the object compounds of this invention, can be produced by subjecting a compound (I) (n=0) to oxidation. The oxidizing agent to be employed here is exemplified by peracid such as m-chloroperbenzoic acid, hydrogen peroxide, peracetic acid, trifluoroperacetic acid or permaleic acid, or sodium bromite, sodium hypachlorite, etc. The solvent to be used for the reaction is exemplified by halogenated hydrocarbon such as chloroform or dichloromethane, ethers such as tetrahydrofuran or diozane, amide such as N,N-dimethylforamide, or water, and these solvents may be used singly or in admixture. The oxidizing agent is used preferably in approximately equivalent or a little excess amount relative to the compound (I) (n=0). Specifically, it is about 1 to about 3 equivalents, more preferably about 1–1.5 equivalent. The reaction temperature ranges usually from that under ice-cooling to about the boiling point of the solvent employed, usually from that under ice-cooling to room temperature, more preferably from about 0° C. to 10° C. The reaction time usually ranges from about 0.1 to about 24 hours, more preferably from about 0.1 to about 4 hours.

Further, the method comprising oxidation by hydrogen peroxide in the presence of a vanadium compound, which is disclosed in European Patent 302720, can be effectively employed.

The object compound (I) produced by the above reaction can be isolated and purified by conventional means, e.g. recrystallization and chromatography.

The compound (I) of this invention may be led to pharmacologically acceptable salts thereof by conventional means, the salts being exemplified by hydrochloride, hydrobromide, hydroiodide, phosphate, nitrate, sulfate, acetate and citrate.

Among the compounds (I), those of n=0 give stable salts, while those of n=1 may exist as an aqueous solution though unstable.

The starting compound (II) can be produced by, for example, the method shown by the following reaction scheme.

$$\underset{(III)}{\overset{R^5}{\underset{}{\bigodot}}\!\!\!\!\underset{\underset{H}{N}}{\overset{N}{\bigvee}}\!\!\!\!S-CH_2\!\!-\!\!\underset{N}{\overset{R^2}{\bigodot}}\!\!\!\!\overset{OR^6}{\underset{}{\bigvee}}\!\!\!\!R^3} \quad \xrightarrow{\text{"acid"}} \quad (II)$$

wherein $R^5$ stands for a substituent on the benzene ring; $R^6$ stands for lower alkyl or aralkyl; $R^2$ and $R^3$ are of the same meaning as defined above.

In the above formula, examples of the substituent on the benzene ring shown by $R^5$ include hydrogen, lower alkoxy, aralkyloxy, halogen and trifluoromethyl.

Examples of the lower alkoxy of $R^5$ include 1–4C alkoxy such as methoxy, ethoxy, propoxy, isopropoxy, butoxy and isobutoxy; examples of aralkyloxy of $R^5$ include benzyloxy and 4-chlorobenzyloxy; and examples of halogen includes fluorine, chlorine, bromine and iodine.

In the above formula, examples of the lower alkyl shown by $R^6$ include 1–5C alkyl such as methyl, ethyl, isopropyl, propyl, butyl, isobutyl, pentyl and neopentyl.

Examples of the aralkyl shown by $R^6$ include benzyl and 4-chlorobenzyl.

This method serves to produce a hydroxy derivative of the general formula (II) by subjecting a compound represented by the general formula (III) to ether linkage severing reaction by acid.

Examples of the acid to be used for the reaction include hydrogen bromide and hydrogen chloride, and examples of the solvent to be used for the reaction include water and acetic acid. The reaction temperature ranges from 20° C. to about the boiling point of the solvent then employed. The reaction time ranges from about one hour to about 100 hours, preferably 3–50 hours.

Compounds represented by the general formula (III) can be produced by conventional methods, for example, those disclosed in European Patent 174726 and 175464, or those analogous thereto.

Pharmacological actions of the compounds of the present invention are described as follows. The role of acid in the occurrence of gastric and duodenal ulcers is well known, and, besides, importance of protecting ability of gastric mucosa has recently been recognized, cf. Miller T. A., Am.J.Physiol., 245, G601 (1983). As a method of determining the protective ability of the gastric mucosa, there is mentioned the one using ethanol-induced gastric mucosal lesions as the index, which was developed by Robert et al.:

Robert A., Gastroenterology 77, 761 (1979) and, by using this method, the action of the compounds of the present invention was examined.

Experimental Method

Male Sprague Dawley rats 7-week old were fasted for 24 hours. These animals were administered test compounds into the stomach by using a gastric tube. After 30 minutes, 1 ml of absolute ethanol was administered orally. At 60 minutes after the administration of ethanol, these animals were sacrificed with carbon dioxide gas. The stomach was removed together with the lower part of the esophagus and duodenum. The esophagus was clipped, 10 ml of 1% formalin solution was instilled into the stomach from the duodenum, and then the duodenum was clipped. The whole stomach was immersed in 1% formalin solution. About 15 minutes later, the stomachs were opened along the greater curvature. The length of of the each lesions which occurred in the gastric antral mucosa was measured under a dissecting microscope with a square-grid eye piece ($\times 10$). The sum total of the length of individual lesions in each animal was measured, and the average value per group was calculated. Based on the difference between the average value of each group and that of the control group, the inhibition rate was determined. The test compounds were all suspended in a 5% gum arabic solution and administered in a volume of 2 ml/kg.

Experimental Results

Using 6 rats per group, 2-[(4-difluoromethoxy-3-methyl-2-pyridyl)methylsulfinyl]benzimidazole was administered in a dose of 1, 3 and 10 mg/kg to determine $ID_{50}$. The $ID_{50}$ was 4.5 mg/kg.

Thus, the compounds of this invention show excellent actions of protecting gastric mucosa.

The toxicity of the compound (I) of this invention is generally low. For example, when the compound used in the above-mentioned experiment for the gastric protecting action was administered orally to mice in a dose of 300 mg/kg, no animals died.

As described previously, the compound (I) of this invention has an anti-ulcer action, antisecretory action and a gastric mucosal protective action. Furthermore, the compound (I) of this invention is of low toxicity and is relatively stable as a chemical substance. The compound (I) of this invention can thus be used for prophylaxis and therapy of peptic ulcers in mammalian animals (e.g. mouse, rat, rabbit, dog, cat and man).

When the compound (I) of this invention is used as an anti-ulcer agent for the therapy of peptic ulcers in mammalian animals, it can be administered orally in a dosage form of capsules, tablets, granules, etc. by formulating with a pharmacologically acceptable carrier, excipient, diluent, etc. The daily dose is about 0.01–30 mg/kg, more preferably about 0.1–3 mg/kg.

Incidentally, the compound (I) (n=0) of this invention is useful as a starting material for producing the compound (I) (n=1).

A sulfinyl derivative (I) (n=1) and its salt are stabilized by evenly contacting with a basic substance which shows basicity (pH of not less than 7) when it is in the form of an 1% aqueous solution or suspension.

Said basic substance includes, among others, a basic inorganic salt (e.g. magnesium carbonate, magnesium hydroxide, magnesium oxide, magnesium metasilicate, precipitated calcium carbonate, sodium hydroxide, sodium biphosphate, potassium hydroxide).

Said basic substance may be used either singly or in combination of two or more species in an amount which may vary depending on the kinds thereof but generally lies within the range of 0.3 to 20 parts by weight, preferably 0.6 to 7 parts by weight, per part by weight of the sulfinyl derivative (I) (n=1) or its salt.

WORKING EXAMPLES

The processes of producing the starting compounds to be employed in the methods of this invention as well as those of producing the compound (I) of this invention are specifically explained by the following Reference Examples and Working Examples, respectively.

REFERENCE EXAMPLE 1

A solution of 2-[(4-methoxy-3-methyl-2-pyridyl) methylthio]benzimidazole (16.6 g) in 47% aqueous solution of HBr (250 ml) was heated for 24 hours under reflux. The reaction mixture was concentrated under reduced pressure. The concentrate was neutralized with a saturated aqueous solution of sodium hydrogencarbonate. The oily portion was separated and subjected to a silica gel column chromatography, eluting with chloroform-methanol (25:2, v/v), to give 2-[(4-hydroxy-3-methyl-2-pyridyl)methylthio]benzimidazole (10.8 g) as colorless powder. $^1$H-NMR($\delta$ ppm in CDCl$_3$): 2.12(3H,s), 4.38(2H,s), 6.43(1H,d,J=7Hz), 7.1–7.3(2H,m), 7.4–7.6(3H,m)

The above-mentioned powder was processed with a hydrogen chloride ethanol solution (8 N) to give crystals of dihydrochloride. Recrystallization from ethanol gave colorless prisms, mp 233°–235° C.

| Elemental Analysis for C$_{14}$H$_{13}$N$_3$OS.2HCl: | | | |
|---|---|---|---|
| Calcd.: | C, 48.84; | H, 4.39; | N, 12.21 |
| Found: | C, 48.59; | H, 4.29; | N, 12.16 |

REFERENCE EXAMPLE 2

A solution of 5-fluoro-2-[(4-methoxy-3-methyl-2-pyridyl)methylthio]benzimidazole (5.5 g) in aqueous 47% HBr (50 ml) was heated for 24 hours under reflux. The reaction mixture was concentrated under reduced pressure. The residual oily substance was neutralized with a saturated aqueous solution of sodium hydrogencarbonate, to which was added ethyl acetate (50 ml) to give 5-fluoro-2-[(4-hydroxy-3-methyl-2-pyridyl)methylthio]benzimidazole (3.2 g, 62%). Recrystallization from ethanol afforded colorless needles, mp 232°–233° C.

| Elemental Analysis for C$_{14}$H$_{21}$N$_3$OSF: | | | |
|---|---|---|---|
| Calcd.: | C, 58.12; | H, 4.18; | N, 14.52 |
| Found | C, 58.00; | H, 3.94; | N, 14.52 |

REFERENCE EXAMPLE 3

By substantially the same procedure as in Reference Example 1, 2-[(4-hydroxy-3-methyl-2-pyridyl)methylthio]-5-trifluroromethylbenzimidazole was obtained as a colorless powdery product. $^1$H-NMR($\delta$ ppm in CDCl$_3$): 2.35(3H,s), 4.41(2H,s), 6.35(1H,d,J=7 Hz), 7.05(1H,d,J=7 Hz), 7.5–7.9(3H,m).

REFERENCE EXAMPLE 4

A solution of 2-[(4-methoxy-3-methyl-2-pyridyl)methylthio]-5-propoxybenzimidazole (5.5 g) in 47% HBr aqueous (50 ml) was heated for 24 hours under reflux. The reaction mixture was concentrated under reduced pressure, and the residual oily substance was neutralized with a saturated aqueous solution of sodium hydrogencarbonate. The oily substance then separated was subjected to a silica gel column chromatography, eluting with chloroform-methanol (10:1, v/v). From the eluate, 5-hydroxy-2-[(4-hydroxy-3- methyl-2-pyridyl)methylthio]benzimidazole (3.2 g, 72%) as a colorless powdery product. $^1$H-NMR($\delta$ ppm in CD$_3$OD): 1.96(3H,s), 4.20(2H,s), 6.37(1H,d,J=7 Hz), 6.75(1H,double d, J=8 and 2 Hz), 6.86(1H,d,J=2 Hz), 7.33(1H,d,J=8 Hz), 7.68(1H,d,J=7 Hz).

REFERENCE EXAMPLE 5

In substantially the same manner as in Reference Example 1, 2-[(3,5-dimethyl-4-hydroxy-2-pyridyl)methylthio]benzimidazole dihydrochloride was obtained, which was recrystallized from methanol to afford colorless prisms, mp 245°–247° C.

| Elemental Analysis for C$_{15}$H$_{13}$N$_3$OS.2HCl: | | | |
|---|---|---|---|
| Calcd.: | C, 50.28; | H, 4.78; | N, 11.73 |
| Found: | C, 49.90; | H, 4.75; | N, 11.48 |

REFERENCE EXAMPLE 6

In substantially the same manner as in Reference Example 1, 2-[(3,5-dimethyl-4-hydroxy-2-pyridyl)methylthio]-5-fluorobenzimidazole dihydrochloride was obtained, which was recrystallized from methanol to afford colorless prisms, mp 228°–230° C.

| Elemental Analysis for C$_{15}$H$_{14}$N$_3$OSF.2HCl: | | | |
|---|---|---|---|
| Calcd.: | C, 47.88; | H, 4.29; | N, 11.17 |
| Found: | C, 47.61; | H, 4.44; | N, 10.91 |

EXAMPLE 1

In N,N-dimethylforamide (DMF) (100 ml) was dissolved 2-[(4-hydroxy-3-methyl-2-pyridyl)methylthio]-benzimidazole (10.5 g). To the solution was added 1,8-diazabicyclo[5,4,0]undec-7-ene (DBU) (7.1 g), to which was introduced chlorodifluoromethane for 3 hours at room temperature. The reaction mixture was poured into water (500 ml), which was subjected to extraction with ethyl acetate. The ethyl acetate layer was washed with water and dried (MgSO$_4$), then the solvent was distilled off. The residue was subjected to a silica gel column chromatography. From the portion eluted with chloroform-methanol (100:1, v/v), 2-[(4-difluoromethoxy-3-methyl-2-pyridyl)methylthio]benzimidazole was obtained (2.5 g, 20%). Recrystallization from ethyl acetate - hexane gave colorless needles, m.p. 99°–100° C.

| Elemental Analysis for $C_{15}H_{13}N_3OSF_2$: | | | |
|---|---|---|---|
| Calcd.: | C, 56.06; | H, 4.08; | N, 13.08 |
| Found: | C, 56.24; | H, 4.04; | N, 13.07 |

EXAMPLE 2

In chloroform (20 ml) - methanol (10 ml) was dissolved 2-[(4-difluoromethoxy-3-methyl-2-pyridyl)methylthio]benzimidazole (2.0 g). To the solution was added dropwise, under ice-cooling, a solution of m-chloroperbenzoic acid (MCPBA) (80%, 1.5 g in chloroform (20 ml). The reaction mixture was washed with a saturated aqueous solution of sodium hydrogencarbonate and water, in that order, then dried (MgSO₄). The solvent was distilled off. The residual solid was subjected to a silica gel column chromatography. From the portion eluted with ethyl acetate - methanol (100:3, v/v), was obtained 2-[(4-difluoromethoxy-3-methyl-2-pyridyl)methylsulfinyl]benzimidazole (1.5 g, 71%). Recrystallization from ethyl acetate—ether gave colorless needles, m.p. 157°–158° C. (decomp.).

| Elemental Analysis for $C_{15}H_{13}N_3O_2SF_2$: | | | |
|---|---|---|---|
| Calcd.: | C, 53.41; | H, 3.88; | N, 12.46 |
| Found: | C, 53.47; | H, 4.05; | N, 12.45 |

EXAMPLES 3 TO 6

In substantially the same manner as in Example 1, the compounds shown in Table 1 were obtained.

TABLE 1

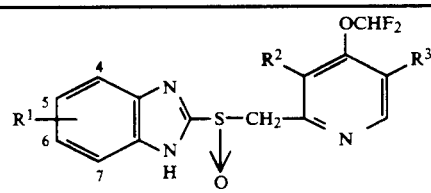

| Ex. No. | $R^1$ | $R^2$ | $R^3$ | mp (°C.) | Recrystallization solvent |
|---|---|---|---|---|---|
| 3 | 5-F | CH₃ | H | 129–130 | ethyl acetate - hexane |
| 4 | 5-CF₃ | CH₃ | H | 149–150 | ethyl acetate - hexane |
| 5 | H | CH₃ | CH₃ | 159–160 | ethyl acetate - hexane |
| 6 | 5-F | CH₃ | CH₃ | 183–184 | ethyl acetate |

EXAMPLE 7

In N,N-dimethylformamide (60 ml) was dissolved 5-hydroxy-2-[(4-hydroxy-3-methyl-2-pyridyl)methylthio]benzimidazole (3.1 g), to which was added 1,8-diazabicyclo[5,4,0]undec-7-ene (3.9 g). To the mixture was introduced chlorodifluoromethane for one hour at room temperature. The reaction mixture was poured into water, which was subjected to extraction with ethyl acetate. The ethyl acetate layer was washed with water, then dried (MgSO₄), followed by distilling off the solvent. The residual oily substance was subjected to a silica gel column chromatography, eluting with chloroform-methanol (20:1, v/v). From the initial fraction of the eluate, 5-difluoromethoxy-2-[(4-difluoromethoxy-3-methyl-2-pyridyl)methylthio]benzimidazole was obtained, followed by recrystallization from ethyl acetate—hexane to afford colorless prisms, mp 181°–182° C.

| Elemental Analysis for $C_{16}H_{13}N_3O_2SF_4$: | | | |
|---|---|---|---|
| Calcd.: | C, 49.61; | H, 3.38; | N, 10.85 |
| Found: | C, 49.46; | H, 3.34; | N, 10.77 |

EXAMPLE 8

From the fraction eluted after 5-difluoromethoxy-2-[(4-difluoromethoxy-3-methyl-2-pyridyl-)methylthio]benzimidazole by the silica gel column chromatography in Example 7, 2-[(4-difluoromethoxy-3-methyl-2-pyridyl) methylthio]-5-hydroxybenzimidazole was obtained, which was recrystallized from ethyl acetate to give colorless needles, mp 214°–215° C.

| Elemental Analysis for $C_{15}H_{13}N_3O_2SF_2$: | | | |
|---|---|---|---|
| Calcd.: | C, 53.40; | H, 3.88; | N, 12.46 |
| Found: | C, 53.28; | H, 3.89; | N, 12.31 |

EXAMPLES 9 TO 12

In substantially the same manner as in Example 2, the compound shown in Table 2 were obtained.

TABLE 2

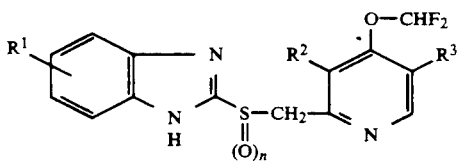

| Ex. No. | $R^1$ | $R^2$ | $R^3$ | mp (decomp.) (°C.) | Recrystallization solvent |
|---|---|---|---|---|---|
| 9 | 5-F | CH₃ | H | 172–173 | ethyl acetate |
| 10 | 5-CF₃ | CH₃ | H | 162–163 | ethyl acetate - hexane |
| 11 | H | CH₃ | CH₃ | 142–143 | ethyl acetate - hexane |
| 12 | 5-F | CH₃ | CH₃ | 163–164 | ethyl acetate - hexane |

What is claimed is:

1. A compound of the formula wherein $R^1$ is hydroxyl, fluorine, or difluoromethoxy, $R^2$ and $R^3$ are independently hydrogen or methyl, and n is 0 or 1, or a pharmacologically acceptable salt thereof.

2. The compound according to claim 1, wherein $R^2$ is methyl.

3. The compound according to claim 1, wherein $R^3$ is hydrogen.

4. The compound according to claim 1, wherein n is 1.

5. The compound according to claim 1, wherein the compound is 2-[(4-difluoromethoxy-3-methyl-2-pyridyl)methylthio]-5-fluorobenzimidazole.

6. The compound according to claim 1, wherein the compound is 2-[(4-difluoromethoxy-3,5-dimethyl-2-pyridyl)methylthio]-5-fluorobenzimidazole.

7. The compound according to claim 1, wherein the compound is 5-difluoromethoxy-2-[(4-difluoromethoxy-3-methyl-2-pyridyl)methylthio]benzimidazole.

8. The compound according to claim 1, wherein the compound is 2-[(4-difluoromethoxy-3-methyl-2-pyridyl)methylthio]-5-hydroxybenzimidazole.

9. The compound according to claim 1, wherein the compound is 2-[(4-difluoromethoxy-3-methyl-2-pyridyl)methylsulfinyl]-5-fluorobenzimidazole.

10. The compound according to claim 1, wherein the compound is 2-[(4-difluoromethoxy-3, 5-dimethyl-2-pyridyl)methylsulfinyl]-5-fluorobenzimidazole.

11. A pharmaceutical composition useful for the treatment of peptic ulcers and gastritis, which contains an effective amount of the compound as claimed in claim 1 and a pharmaceutically acceptable carrier.

* * * * *